United States Patent [19]

Henderson, Jr. et al.

[11] 4,395,369

[45] Jul. 26, 1983

[54] MANUFACTURE OF ISOCYANATE

[75] Inventors: William A. Henderson, Jr.; Balwant Singh, both of Stamford, Conn.

[73] Assignee: American Cyanamid Company, Stamford, Conn.

[21] Appl. No.: 355,945

[22] Filed: Mar. 8, 1982

Related U.S. Application Data

[63] Continuation-in-part of Ser. No. 331,696, Dec. 17, 1981, Pat. No. 4,361,518.

[51] Int. Cl.$^3$ ............................................. C07C 118/00
[52] U.S. Cl. .................................................. 260/453 P
[58] Field of Search ...................................... 260/453 P

[56] References Cited

U.S. PATENT DOCUMENTS 3,290,350 12/1966 Hoover ............................ 260/453 P
4,130,577 12/1978 Nagato et al. ................... 260/453 P

*Primary Examiner*—Dolph H. Torrence
*Attorney, Agent, or Firm*—Steven J. Hultquist

[57] ABSTRACT

A process for production of tertiary aralkyl isocyanates by reaction at low temperatures of the corresponding halides with an excess of isocyanic acid. Manufacture of TMXDI is specifically contemplated.

12 Claims, No Drawings

MANUFACTURE OF ISOCYANATE

This application is a continuation-in-part of application Ser. No. 331,696, filed Dec. 17, 1981, U.S. Pat. No. 4,361,518.

This invention relates to the manufacture of tertiary aralkyl isocyanates, particularly diisocyanates such as the tetramethylxylylenediisocyanates (TMXDI) and in particular provides a process for the preparation of such isocyanates from the corresponding halides.

Isocyanates are well known and valuable class of compounds. In particular meta-and para-TMXDI are useful for reaction with a wide variety of polyols to give polyurethanes which are either rigid or flexible and which can be endowed with a wide variety of properties. Thus such polyurethanes can be formed into rigid and flexible foamed articles, sheets, high density sheets and articles of various shapes. The light stability of the polyurethanes makes them extremely useful in coating and other applications where light stability is desirable, e.g. light stable RIM elastomers.

Tertiary mono- and polyisocyanates, such as TMXDI have heretofore been manufactured by phosgenation of the corresponding organic amines, by reaction of the corresponding olefins with isocyanic acid (U.S. Pat. No. 3,290,350) and by reaction of the corresponding halides with an alkali metal isocyante (U.S. Pat. No. 4,130,577).

The phosgenation route suffers disadvantages from the commercial standpoint in that phosgene itself is an unsafe material and difficult to handle. In addition the organic amines are difficult to produce. The olefin route suffers the disadvantages that the yields are poor and that large amounts of olefin and isocyanic acid are lost through selfpolymerization. On the other hand, while the reaction of the halide with the alkali metal isocyanate can provide high yields, the reaction times are long and the halogen is completely lost as the alkali metal halide, recoverable only at great expense.

It is thus an important object of this invention to provide a process for the production of tertiary aralkyl isocyanates and particularly diisocyanates which can be made to operate on a commercially economic basis with high yields of the desired product. It is further object of the invention to provide such a process which can be operated at relatively fast rates conducive to continuous production. It is yet another object of this invention to provide such a process in which excess reactants are readily recoverable.

Thus in accordance with this invention tertiary aralkyl mono- and polyisocyanates are produced by reaction of the corresponding halide with isocyanic acid, HNCO, utilizing an excess of isocyanic acid in solution in a solvent or mixture of solvents, such as an aromatic hydrocarbon, halogenated hydrocarbon or aliphatic hydrocarbon solvent or solvents. Among the suitable solvents are toluene, xylenes, methyl napthalenes, chlorobenzene, orthodichlorobenzene, heptane, benzene, methylene dichloride, haloalkanes and the like. Generally the solvent is an aprotic or non-polar solvent which is a solvent both for the starting halide and for the isocyanic acid.

The reaction proceeds at relatively low temperatures, rapidly in the presence of suitable catalyst. The reaction will proceed, however somewhat more slowly, even in the total absence of catalyst and even at relatively low temperatures. The preferred catalyst is $ZnCl_2$. A large number of catalysts can be used besides $ZnCl_2$. These can be added to the reaction mixture either as a solid compound or dissolved in a small amount of a suitable solvent.

Preferably the reaction is carried out at temperatures on the order of $-10°$ to $10°$ C. Higher and lower temperatures can be utilized. Higher temperatures, however, favor polymerization of isocyanic acid to form solids while lower temperatures reduced the speed of reaction. Reaction times are typically in the range of 10 seconds to 4 hours.

The reactants should be substantially anhydrous. Even small amounts of water above approximately 200 ppm tend to make the reaction sluggish.

Tertiary aralkyl halides which can be reacted with isocyanic acid in accordance with this invention are characterized by a tertiary carbon atom having a halogen substituent which carbon atom is attached to an aromatic nucleus. The aromatic moiety can have a monocyclic, a polycyclic or a fused ring structure and can have non-reactive substituents such as halogen atoms and alkyl, haloalkyl and alkoxy groups, and preferably has one or more other reactive tertiary, halogen substituted carbon atoms as substituents. The tertiary aralkyl halides useful in accordance with the invention are described by the generalized formula

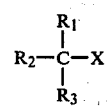

in which:

X is a halogen such as Cl, Br or I;

$R_1$ and $R_2$ can be the same or different and are normal, branched or cycloalkyl, phenyl, naphthyl or higher aryl groups or are joined to give cyclic substituents yielding compounds such as

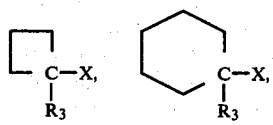

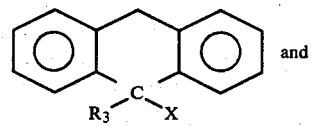

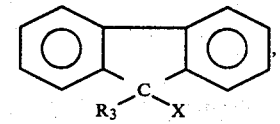

and $R_3$ is an aromatic group including phenyl, naphthalyl, higher fused ring aryl, biphenyl, aralkyl, such as

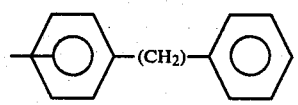

and poly cyclic aryl groups joined by linkages such as

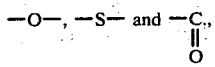

and such aromatic groups having substituents such as halogen atoms, methyl or methoxy groups and

substituents.

Such halide compounds and particularly the chlorides are readily obtained in high yield by synthesis from the corresponding olefins. The reaction of the halide with excess isocyanic acid results in the formation of the isocyanate and hydrogen halide. The latter combines with excess isocyanic acid to produce carbamoyl halide. Excess isocyanic acid and carbamoyl halide are recoverable by distillation or other means and can be recycled.

In addition to zinc chloride, zinc bromide and zinc iodide are effective catalysts.

Other zinc catalysts which have been found effective in the process of this invention are zinc neodecanoate, zinc fluoride, zinc dodecylbenzenesulfonate and zinc bromide.

Other Lewis acids, such as bismuth trichloride and bismuth tribromide have also been found to exhibit substantial catalytic activity. Ferric chloride and stannous chloride have shown weak catalytic activity. On the other hand boron trichloride mercuric chloride, aluminum tribromide, aluminum trichloride, ferrous chloride zirconium chloride and cuprous chloride have been found to exhibit little or no catalytic activity. Preferably the catalyst is added in solution form to a precooled solution of the isocyanic acid over the relatively short time required for reaction for example, 90 seconds. All catalysts showing activity have been found to be soluble in ether or acetone and have been used in solution. The preferred solvents for zinc chloride catalyst are diethylether or ketones such as di-i-butylketone or 2-octanone. Basic solvents, such as pyridine, are to be avoided, as the isocyanic acid is almost completely lost in polmerization to cyanuric acid.

The proportion of isocyanic acid is generally in excess of the halide on a stoichiometric basis and preferably is 5 moles of isocyanic acid per halogen atom, but can be varied over a wide range, e.g. from 2 to 20 moles per halogen atom. The proportion of the preferred catalyst is preferably about 0.025 mole per halogen atom but can be varied between 0.0005 and 0.25 mole with good results.

For a more complete understanding of the practical application of this invention reference is made to the following examples:

EXAMPLE I

Para di (2-chloroisopropyl) benzene was prepared in 2 M solution in toluene dried over 3 Å molecular sieve. A 3.8 M solution of isocyanic acid (HNCO) was also prepared in toluene and dried over molecular sieve. A zinc chloride catalyst was prepared in a 1 M solution in anhydrous diethyleter.

11.5 mmoles of isocyanic acid solution was placed in a 20 ml reaction vessel cooled in an ice bath to 0° C. Agitation was provided using a magnetic stirrer. Two mmoles and 0.1 mmoles of the para-di(2-chloroisopropyl) benzene and zinc chloride solutions, respectively, were simultaneously added using two separate syringe pumps over the course of 90 seconds. The reaction mixture was stirred and kept in the ice bath over the whole course of the reaction period. Aliquots of the reaction were then removed and analyzed.

Analysis for the organic products was by gas chromatography and for the isocyanic acid by titration. The isocyanic acid analysis was conducted by extracting an aliquot of the reaction mixture with sodium hydroxide solution to give sodium isocyanate and conversion of the isocyanate to ammonia by reaction with hydrochloric acid. The solution was then basified and ammonia determined with an ammonia specific electrode. The by-product carbamoyl chloride was also converted to ammonia and analyzed as such.

The results are shown in Table I. 98% of the dichloride was consumed with yields of 9% of the monochloride-monoisocyanate and 79% of the diisocyanate, (TMXDI), based on the initial dichloride. The yield of diisocyanate was 87%, based on the isocyanic acid consumed. Four additional runs repeating the procedure of Example I gave similar results with yields of diisocyanate from 75 to 76%, based on the dichloride consumed.

EXAMPLES II–XI

Results Shown in Table I

EXAMPLE II

The procedure of Example I was repeated, except the zinc chloride solution was added all at once and the temperature was 45° C.

EXAMPLE III

The procedure of Example I was repeated, except that the zinc chloride was added last and all at once. The results shown in Table I are an average of three runs.

EXAMPLE IV

The procedure of Example III was repeated but diluted with toluene from 4.4 ml to 16.4 ml.

EXAMPLE V

The procedure of Example I was repeated except the zinc chloride was in acetone solution.

EXAMPLE VI–VIII

The procedure of Example I was repeated, except the proportion of isocyanic acid to para-TMXDC was 4.2 (Example VI), 8.1 (Example VII) and 12.2 (Example VIII).

EXAMPLE IX AND X

The procedure of Example I was repeated, except the amount of zinc chloride was 0.05 moles (Example IX) and 0.2 mmoles (Example X)

EXAMPLE XI

The procedure of Example I was repeated, except methylene chloride was substituted as the solvent for the dichloride and isocyanic acid.

TABLE I

| Example No. | Unreacted Dichloride | Yield, Wt. % Chloro-iso-cyanate | TMXDI | Yield, Wt. % Based on Consumption of Dichloride | HNCO |
|---|---|---|---|---|---|
| I | 2 | 9 | 79 | 80 | 87 |
| II | 8 | 24 | 24 | 26 | 10 |
| III | 3 | 10 | 55 | 56 | — |
| IV | 50 | 18 | 3 | 6 | — |
| V | 17 | 24 | 41 | 50 | — |
| VI | 27 | 20 | 21 | 29 | 41 |
| VII | 13 | 20 | 38 | 39 | 50 |
| VIII | 9 | 20 | 60 | 66 | 67 |
| IX | 2 | 14 | 67 | 68 | — |
| X | 4 | 12 | 73 | 76 | — |
| XI | 7 | 20 | 58 | 62 | 62 |

Increasing the scale of the process lengthened the time of the reaction as the dichloride and catalyst had to be added more slowly to hold the temperature under 10° C. At 20 times the scale with addition of dichloride and zinc chloride over ten minutes, maximum temperature was 5° C., and the diisocyanate yield was 72%, 75% based on the dichloride consumed.

EXAMPLE XII

Meta-di-(2-chloroisopropyl) benzene was reacted with isocyanic acid in toluene solution, following the procedure of Example I, using 2 mmoles of the dichloride and a ratio of dichloride to isocyanic acid to zinc chloride of 1:6.5:0.05 in a bath maintained at −10° C. with addition of catalyst and dichloride over a 1.5 minute period of time. The yield of an average of four runs was 8% of the monochloride-monoisocyanate and 85% of the diisocyanate, 92% diisocyanate calculated on the basis of dichloride consumed, and 86% calculated on the basis of isocyanic acid consumed.

EXAMPLE XIII

The procedure of Example I was followed omitting the catalyst with the following results:

TABLE II

| Time, Hrs. | Yield, % Chloroisocyanate | TMXDI | TMXDI Yield, % Bases on Consumption of Dichloride | HNCO |
|---|---|---|---|---|
| 0.06 | 0.3 | 0 | 0 | 0 |
| 1 | 28 | 1 | 2 | — |
| 2 | 38 | 5 | 7 | 11 |
| 3.5 | 40 | 10 | 12 | — |
| 5 | 40 | 14 | 16 | 21 |

EXAMPLE XIV

A continuous, backstirred reactor was set up with provision for addition of a reactant stream of isocyanic acid and para-di(2-chloroisopropyl)benzene in toluene solution and a zinc chloride catalyst stream in ether utilizing the concentrations and proportions of Example I. The reactor was provided with agitation by a magnetic stirrer, and was cooled with a salt/ice bath held at −10° C. The dichloride and isocyanic acid streams were premixed just before entering the reactor to minimize crystallization of the dichloride upon contact with the cold reactor. The temperature of the reaction mixture was 0° C., and the residence time was 3.6 minutes. The effluent was diluted with cold toluene for chromatographic analysis or was extracted with caustic solution for analysis for isocyanic acid. The results were as follows:

TABLE III

| Residence Times | Temp. °C. | Yields, % Chloroiso-cyanate | TMXDI | Yields, % based on Consumption of Dichloride | HNCO |
|---|---|---|---|---|---|
| 3 | 0 | 11 | 80 | 94 | 68 |
| 4 | 1 | 11 | 78 | 92 | 64 |
| 6 | 1 | 11 | 78 | 92 | 63 |

EXAMPLE XV

One mmole of zinc chloride dietherate in toluene was added to a solution of 20 mmoles of p-di(2-bromoisopropyl) benzene and 130 mmoles of isocyanic acid in toluene (total volume 40 ml.) with stirring over a ten minute period at −10° to −2° C. After a further 5 minutes of stirring, the mixture was filtered to remove by-product white solids and analyzed. The yield of p-tetramethylxylylenediisocyanate was 80%, and that of the bromisocyanate 10%. The products were isolated from polymeric material and white solids by rapid distillation in a wiped film evaporator, and the diisocyanate then isolated in pure form by distillation at low pressure. The diisocyanate (p-TMXDI) melted at 74°–76° C.

EXAMPLE XVI

The procedure of Example XV was repeated substituting m-di(2-bromoisopropyl) benzene for the para isomer, except that the reaction mixture was stirred for an additional 15 minutes after addition of the zinc catalyst, and the catalyst used was zinc chloride dissolved in diisobutylketone. The yields of the di- and mono-isocyanates were 75 and 12%, respectively. The products were isolated in the same way as in Example XV.

EXAMPLE XVII 2,6-Di(2-chloroisopropyl) naphthalene was prepared by passing a stream of anhydrous hydrochloric acid into a suspension of 0.18 moles of 2,6-diisopropenylnaphthalene in toluene stirred at −4° until NMR showed that conversion to the dichloride was complete. 1.40 moles of 4.5 M isocyanic acid in toluene was added to the dichloride, and the solution was stirred at −10° to −2° while 0.01 moles of zinc chloride etherate in toluene was added over 20 minutes. The reaction mixture was stirred an additional 30 minutes and then filtered to remove solids. The solvent and low boiling materials was removed in vacuo to leave a waxy solid. This was refluxed for 1 hour in hexane and then cooled to room temperature. The resulting solid was filtered and air dried to give 0.14 moles (75%) of α,α,α',α'-tetramethyl-2,6-dimethynaphthalene-α,α'-diisocyanate, m.p. 85.5°–86°.

EXAMPLE XVIII p-α,α'-Dimethyl-α,α'-dibutylxylylene-α,α'-dichloride is prepared from α,α'-dimethyl-β,β'-dipropyl-p-divinylbenzene and reacted with isocyanic acid as in Example XVII. The product diisocyanate is isolated by distillation at low pressure in 73% yield. It shows an intense band in the infrared at 2250 cm$^{-1}$ (isocyanate).

EXAMPLE XIX p-Dicyclohexylbenzene-α,α'-dichloride is prepared and reacted with isocyanic acid as in Example XVII.

The solid diisocyanate product is isolated by distillation at low pressure in 65% yield.

EXAMPLE XX

α,α,α',α'-Tetramethyl-4,4'-dimethylbiphenyl α,α'-diisocyanate is prepared by the reaction of isocyanic acid with the corresponding dichloride in the same manner as in Example XVII. The product is isolated by distillation in 68% yield.

EXAMPLE XXI p-α,α,α',α'-Tetramethyl-2-chloro-xylylene-α,α' dichloride is prepared by passing anhydrous hydrochloric acid into a suspension of the corresponding diolefin 1,4-diisopropenyl-2-chlorobenzene in toluene as in Example XVIII. The diisocyanate is prepared by reaction of the dichloride with isocyanic acid in the same way as in Example XVIII, and the product is obtained in 77% yield.

EXAMPLE XXII

α,α,α',α'-Tetramethyl-4,4'-dimethyldiphenylether-α,α'-diisocyanate is prepared in 70% yield by the reaction of the corresponding dichloride with isocyanic acid as in Example XVIII. The product, isolated by distillation shows an isocyanate peak in the infrared at 2250 cm$^{-1}$.

We claim:

1. A process for the production of tertiary aralkyl isocyanates which comprises reacting a halide of the formula

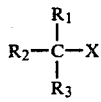

in which X represents a halogen atom, R$_1$ and R$_2$ represent the same or different hydrocarbon radicals selected from normal, branched and cyclic alkyl groups, and phenyl, naphthalyl and higher aryl groups, and can be joined to form substituents forming cyclic compounds, such bivalent substituents being selected from—(CH$_2$)$_n$—where n is an integer from 3 to 5,

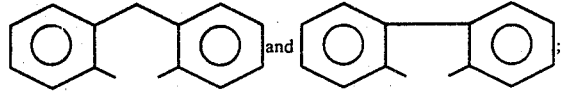

and R$_3$ represents an aromatic hydrocarbon groups selected from phenyl, naphthalyl, higher fused ring aryl and biphenyl groups, polycyclic aromatic hydrocarbon groups of the formula

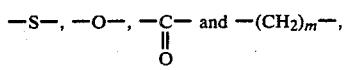

in which Y represents a bivalent radical selected from $$-S-, -O-, -\underset{\underset{O}{\|}}{C}- \text{ and } -(CH_2)_m-,$$

wherein m is an integer from 1 to 3, and such aromatic groups having halogen, methyl, methoxy substituents or substituents of the formula

with a stoichiometric excess of isocyanic acid in a solution in a solvent for said halide and isocyanic acid.

2. A process according to claim 1 in which said reaction is carried out in the presence of a catalyst effective to promote the reaction of halide and isocyanic acid to form the isocyanate.

3. A process according to claim 1 in which the catalyst is zinc chloride.

4. A process according to claim 1 or 3 in which the solvent is toluene.

5. A process according to claim 1 or 3 in which the halide is a di(2-chloroisopropyl) benzene.

6. A process according to claim 1 or 3 in which the reaction temperature is between −10° and 10° C.

7. A process according to claim 1 or 3 in which the proportion of isocyanic acid is from 2 to 10 moles per halogen atom of the halide.

8. A process according to claim 1 or 3 in which the solvent is methylene dichloride.

9. A process according to claim 5 in which the halide is para-di(2-chloroisopropyl) benzene.

10. A process according to claim 5 in which the halide is meta-di(2-chloroisopropyl) benzene.

11. A process according to claim 1 or 3 in which the halide is a bromide.

12. A process according to claim 1 or 3 in which the halide is a di-chloroisopropylnaphthalene.

* * * * *